United States Patent [19]

Miller

[11] Patent Number: 4,465,788

[45] Date of Patent: Aug. 14, 1984

[54] OLEFIN OLIGOMERIZATION WITH AN ACTIVATED CATALYST

[75] Inventor: Stephen J. Miller, San Francisco, Calif.

[73] Assignee: Chevron Research Company, San Francisco, Calif.

[21] Appl. No.: 416,790

[22] Filed: Sep. 10, 1982

[51] Int. Cl.³ .......................... B01J 27/02; B01J 37/12
[52] U.S. Cl. ..................................... 502/217; 502/38; 502/52; 585/531
[58] Field of Search .................................. 252/416, 440

[56] References Cited

U.S. PATENT DOCUMENTS

| | | | |
|---|---|---|---|
| 2,225,782 | 12/1940 | Ipoliff et al. | 252/416 |
| 2,732,329 | 1/1956 | Doumani | 252/440 X |
| 2,794,842 | 6/1957 | Hogan et al. | 252/440 X |
| 3,442,964 | 5/1969 | Oldham | 260/671 |
| 3,959,400 | 5/1976 | Lucki | 260/683.15 |
| 4,318,801 | 3/1982 | Lese et al. | 252/440 X |

*Primary Examiner*—Delbert E. Gantz
*Assistant Examiner*—William G. Wright
*Attorney, Agent, or Firm*—S. R. La Paglia; V. J. Cavalieri

[57] ABSTRACT

An olefin oligomerization catalyst containing nickel sulfate on a porous support, activated by calcining in an oxidizing atmosphere, followed by inert gas treatment at a lower but elevated temperature, is useful for oligomerizing propylene and butenes.

5 Claims, No Drawings

OLEFIN OLIGOMERIZATION WITH AN ACTIVATED CATALYST

BACKGROUND OF THE INVENTION

The present invention is in the field of olefin oligomerization. More specifically, the present invention relates to oligomerization of olefins with an activated catalyst.

Oligomers of lower alkenes (ethene, propene, the butenes and the pentenes) are commercially useful as, for example, relatively high-octane components of motor fuels, and as intermediates in the production of surfactants.

The use of nickel sulfate associated with a porous, inorganic oxide such as alumina for catalyst purposes in olefin oligomerization has been suggested. See, for example, U.S. Pat. No. 2,794,842, which describes the use of nickel sulfate supported on silica, alumina, silica-alumina and kieselguhr. This patent states that a nickel sulfate catalyst should be activated by heating in an oxygen-containing atmosphere at a temperature of 800°–1100° F.

U.S. Pat. No. 3,959,400 describes the dimerization of $C_2$ to $C_4$ light olefins using a nickel sulfate catalyst which has been activated by calcination at a temperature of 750°–1150° F. in an inert, oxygen-free, nonreducing atmosphere. This patent describes the regeneration of a nickel sulfate catalyst by (a) purging overnight at 550° F. with helium, (b) replacing helium with air at 50 cc/minute/cc of catalyst, (c) heating rapidly in air to 950° F., (d) holding for 20 minutes at 950° F., and (e) replacing air with helium for 2 hours at 950° F.

U.S. Pat. No. 3,442,964 describes the dimerization of olefins using nickel sulfate associated with a synthetic cracking catalyst such as silica-alumina. This patent teaches that the dimerization catalyst is activated initially by heating in "inert gas", nitrogen or air to temperatures in the range of 350°–850° C., with the use of air being preferred for activation. It describes the activation of a catalyst consisting of nickel nitrate on silica-alumina by heating in air at 550° C. after which the air is replaced with nitrogen and the catalyst is cooled to dimerization reaction temperature.

SUMMARY OF THE INVENTION

In one embodiment, the present invention relates to a method for activating a catalyst including nickel sulfate associated with a porous, refractory, inorganic oxide, which comprises: contacting the catalyst with a gas containing oxygen at a temperature in the range from about 750° F. to about 1150° F. for at least 2 hours; and contacting the resulting catalyst with an inert gas at a temperature of about 350° F. to about 750° F. for at least 1 hour.

In another embodiment, the present invention relates to a process for oligomerizing a lower olefin in a lower olefin feed comprising: contacting the feed with a catalyst including nickel sulfate associated with a porous, inorganic oxide at oligomerization conditions, the catalyst having been previously activated by contacting the catalyst with a gas containing oxygen at a temperature in the range from about 750° F. to about 1150° F. for at least 2 hours; and contacting the resulting catalyst with an inert gas at a temperature of about 350° F. to about 750° F. for at least 1 hour.

I have found that a nickel sulfate-alumina oligomerization catalyst can be activated in a very commercially practical manner, without the use of an inert gas at extremely high temperatures, taught as necessary in the prior art. This is accomplished according to my invention by the use of a two-stage heat treatment, first with an oxygen-containing gas at 750°–1150° F., and then with an inert gas at a lower temperature of about 350°–750° F. The resulting nickel sulfate catalyst is highly active and selective for dimerizing lower olefins.

DETAILED DESCRIPTION OF THE INVENTION

The term "lower olefin", as used herein, means the $C_2$–$C_4$ alkenes, ethene, propene, 1-butene, 2-butene, and isobutylene.

The term "inert gas", as used herein, means a substantially nonreactive, substantially nonoxidizing, substantially nonreducing gas or gas mixture. Examples are nitrogen, helium, argon and mixtures thereof.

The Catalyst

The catalyst employed in the present invention is nickel sulfate associated with a porous, refractory, inorganic oxide. Examples of suitable porous, refractory, inorganic oxides are alumina, silica, titania, magnesia, zirconia, boria, and the like, and mixtures of two or more of these inorganic oxides. Alumina is a strongly preferred inorganic oxide for use in the present catalyst. Gamma and eta aluminas are particularly preferred supports.

The refractory oxide component of the catalyst is associated with a nickel sulfate component. The nickel sulfate may be deposited onto shaped particles of the refractory, inorganic oxide, as by impregnation. Nickel sulfate may be formed by first associating another nickel compound such as the chloride with the refractory, inorganic oxide component, and then converting the nickel component to sulfide or sulfate form. The sulfide form can then be converted to the sulfate form by oxidation. Nickel compounds may be associated with the refractory inorganic oxide by cogellation, comulling or other convenient techniques. A preferred method of combining the nickel component with the refractory oxide component is by impregnation of previously shaped and sized particles of alumina with a nickel sulfate solution.

After calcination in air, the catalyst should contain about 0.5 weight percent to about 8 weight percent of nickel and about 0.25 weight percent to about 4 weight percent of sulfur.

Activation Procedure

After preparation, the nickel sulfate-alumina catalyst is activated for use in oligomerization. The first step of activation is heat treatment (calcination) in an oxygen-containing gas (i.e., a gas including $O_2$) at a temperature in the range from about 750° F. to about 1150° F. Preferably, the calcination is carried out at a temperature between 850° F. and 1050° F. Air is the preferred oxygen-containing gas. The heat treatment in the oxygen-containing gas is continued for at least 2 hours, and preferably for at least 4 hours. Continuous passage of a flowing stream of heated, oxygen-containing gas over the catalyst is a preferred mode for calcining.

The second step in the catalyst activation procedure is treatment of the catalyst at a lower, but still elevated, temperature with an inert gas. The inert gas treatment is carried out at a temperature in the range from about 350° F. to about 750° F. Preferably, the temperature is maintained between about 450° F. and 750° F. Nitrogen is a preferred inert gas. The heat treatment with inert gas is continued for at least 1 hour, and preferably for at least 2 hours. Preferably, the treatment includes continuous flow of the stream of inert gas through a bed of the catalyst being treated.

Oligomerization Process

The activated nickel sulfate-alumina catalyst is suitable for oligomerization of a variety of unsaturated hydrocarbons. As used herein, the term "oligomerize" includes, without limitation, dimerization and codimerization. The catalyst is especially suitable for oligomerization of lower mono-olefins. A preferred use of the catalyst is for dimerization and codimerization of propene and butenes. Suitable lower olefins for inclusion in olefin feeds are one or more of the mono-olefins ethene, propene, 1-butene, 2-butene and isobutylene. In cases where the lower olefin feed contains more than one species of oligomerizable olefin, the preferred catalytic use of the catalyst will include both dimerization of each olefin species and codimerization of the different olefin species. The lower olefin feed employed in the process may suitably contain hydrocarbons other than alkenes, such as paraffins. The lower olefin feed may, for example, include lower mono-olefins diluted with lower paraffins such as propane, n-butane and isobutane. Suitable feeds are often available in petroleum refineries from normally gaseous catalytic hydrocarbon cracking by-products.

Oligomerization conditions used in the oligomerization process of this invention include a temperature in the range from about 50° F. to about 250° F. An oligomerization temperature in the range from about 90° F. to 180° F. is preferred. Useful pressures are generally between about 200 psig and about 800 psig, with preferred oligomerization pressures being between about 300 psig and 600 psig. A pressure sufficient to maintain oligomerizable lower alkenes in the light olefin feed in the liquid phase is strongly preferred. A liquid hourly space velocity (LHSV) in the range of about 0.5 to about 10 per hour is suitable. An LHSV within the range from about 1 to about 3 per hour is preferred. The catalyst may be employed in the form of a fixed bed, moving bed, slurry, fluidized bed or other convenient mode of contact. A fixed bed operation in which the feed is passed downwardly or upwardly through a bed of the catalyst is preferred. Reaction vessels and other equipment suitable for carrying out the catalyst activation and the oligomerization process are well known to those skilled in the art.

EXAMPLES

The following examples illustrate a preferred mode for preparing and activating a nickel sulfate-alumina catalyst, and for using the catalyst to oligomerize a lower olefin feed. The examples also demonstrate the surprisingly effective results obtained when oligomerizing olefins using a catalyst activated in accordance with the present invention.

EXAMPLE 1

A nickel sulfate-alumina catalyst was prepared. Alumina was peptized with nitric acid, neutralized with ammonia, and shaped by extrusion. After drying, the alumina was calcined at 850° F. for 8 hours. The calcined particles were impregnated with an aqueous nickel sulfate solution, used in sufficient amount to provide 4 weight percent nickel in the catalyst after drying of the catalyst. The impregnated catalyst was then dried at 250° F. for 24 hours.

EXAMPLE 2

A sample of the catalyst prepared as described in Example 1 was activated in accordance with the present invention by first calcining in air at 850° F. for 6 hours and then calcining in nitrogen at 450° F. for 1 hour.

EXAMPLE 3

The sample of catalyst activated as described in Example 2 was employed to dimerize a light olefin feed consisting of propylene. Oligomerization conditions employed included a temperature of 80° F., a pressure of 600 psig, and an LHSV of 1.7 per hour. The propylene conversion levels obtained at various times onstream are shown in Table 1.

TABLE 1

| On-Stream Time and Conversion Level | |
|---|---|
| Time On-Stream (hours) | Conversion Level (weight percent) |
| 13 | 95.9 |
| 17 | 95.6 |
| 27 | 95.6 |
| 33 | 95.9 |
| 38 | 95.8 |
| 42 | 95.7 |
| 47 | 95.2 |

EXAMPLE 4

Various catalyst activation procedures were carried out on the catalyst manufactured as described in Example 1 in order to compare these other activation procedures to the activation procedure according to the invention, employed on Catalyst No. 1 as described in Example 2.

A. Catalyst No. 2 was activated by heating in air for 8 hours at 450° F. Catalyst No. 2 was run at oligomerization conditions substantially identical to those used with Catalyst No. 1 in Example 3 except that conversion in the run using Catalyst No. 2 was measured after 19 hours on-stream.

B. Catalyst No. 3 was activated by heating in air for 8 hours at 650° F. Catalyst No. 3 was run at oligomerization conditions substantially identical to those used with Catalyst No. 1 except that conversion in the run using Catalyst No. 3 was measured after 16½ hours on-stream.

C. Catalyst No. 4 was activated by heating in nitrogen for 4 hours at 450° F. Catalyst No. 4 was run at conditions substantially identical to those used with Catalyst No. 1 except that Catalyst No. 4 was run initially at an LHSV of 1 for 28 hours and then the LHSV was increased to 1.7. Catalyst No. 4 was also run at a higher dimerization temperature of 88° F.

D. Catalyst No. 5 was activated by heating in nitrogen for 8 hours at 650° F., and was run at oligomerization conditions substantially identical to those used in running Catalyst No. 1.

E. Catalyst No. 6 was activated by heating in nitrogen for 8 hours at 850° F., and was run at oligomerization conditions substantially identical to those used with Catalyst No. 1 in Example 3.

F. Catalyst No. 7 was activated by first heating in air for 4 hours at 650° F., and then in nitrogen for 1 hour at 850° F. Catalyst No. 7 was run at oligomerization conditions substantially identical to those used with Catalyst No. 1 as described in Example 3.

G. Catalyst No. 8 was activated by first heating in air for 8 hours at 850° F., and then in nitrogen for 1 hour at 850° F. Catalyst No. 8 was run at oligomerization conditions substantially identical to those used with Catalyst No. 1 as described in Example 3, except that the conversion in the run using Catalyst No. 8 was measured after 17 hours on-stream.

H. Catalyst No. 9 was activated by first heating in air for 8 hours at 1050° F., and then for 1 hour in nitrogen at 850° F. Catalyst No. 9 was run at oligomerization conditions substantially identical to those used with Catalyst No. 1 as described in Example 3, except that Catalyst No. 9 was run at a higher space velocity of 2.5 LHSV.

Each of the Catalyst Nos. 2–9 were employed for propylene dimerization at essentially the same conditions as used with Catalyst No. 1 in Example 3. The results for propylene conversion using each of the Catalyst Nos. 1–9 are shown in Table 2. Results for conversion are measured for each catalyst after about 42 hours of continuous use, except as discussed above.

TABLE 2

| Conversion With Various Activation Procedures | |
|---|---|
| Catalyst No. | Propylene Conversion (weight percent) |
| 1 | 95.7 |
| 2 | <5 |
| 3 | <5 |
| 4 | 9 |
| 5 | 67 |
| 6 | 96 |
| 7 | 98 |
| 8 | 99.2 |
| 9 | 99 |

What is claimed is:

1. A method for activating a catalyst consisting of nickel sulfate associated with a porous, refractory, inorganic oxide, which consists essentially of:
   (a) contacting said catalyst with a gas containing free oxygen at a temperature in the range from about 750° F. to about 1150° F. for at least 2 hours; and
   (b) contacting the resulting catalyst with an inert gas at a temperature of about 350° F. to about 750° F. for at least 1 hour.

2. A method in accordance with claim 1 wherein said porous, inorganic oxide is alumina.

3. A method in accordance with claim 2 wherein said alumina is selected from gamma alumina and eta alumina.

4. A method in accordance with claim 1 wherein said catalyst is contacted with said free oxygen-containing gas at a temperature in the range from about 850° F. to about 1050° F.

5. A method in accordance with claim 1 wherein said catalyst is contacted with said inert gas at a temperature in the range from about 450° F. to about 750° F.

* * * * *